United States Patent
Fuhrman et al.

(10) Patent No.: US 7,367,335 B2
(45) Date of Patent: May 6, 2008

(54) THERAPEUTIC AGENT DELIVERY DEVICE AND METHOD

(75) Inventors: Bradley P. Fuhrman, Buffalo, NY (US); Mark S. Dowhy, Buffalo, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 318 days.

(21) Appl. No.: 10/610,210

(22) Filed: Jun. 30, 2003

(65) Prior Publication Data

US 2004/0003808 A1 Jan. 8, 2004

Related U.S. Application Data

(60) Provisional application No. 60/392,314, filed on Jun. 28, 2002.

(51) Int. Cl.
*A61M 15/00* (2006.01)
*A61M 11/00* (2006.01)
*A61M 16/00* (2006.01)

(52) U.S. Cl. .......... 128/203.15; 128/200.24; 128/200.14; 128/203.12; 128/204.18

(58) Field of Classification Search .......... 128/200.14, 128/200.24, 203.12, 204.22, 205.12, 204.18, 128/205.28, 203.25, 200.16, 200.18, 200.21, 128/200.22, 910, 911
See application file for complete search history.

(56) References Cited

U.S. PATENT DOCUMENTS

| | | |
|---|---|---|
| 1,693,730 A | 12/1928 | Schroder |
| 3,396,723 A | 8/1968 | Freytag |
| 4,127,121 A | 11/1978 | Westenskow et al. |
| 4,354,536 A | 10/1982 | Moss |
| 4,466,433 A | 8/1984 | Robbins |
| 4,543,951 A | 10/1985 | Phuc |
| 4,674,491 A | 6/1987 | Brugger et al. |
| 4,719,910 A | 1/1988 | Jensen |
| 4,747,402 A | 5/1988 | Reese et al. |
| 4,753,245 A | 6/1988 | Gedeon |
| 4,805,612 A | 2/1989 | Jensen |
| 4,821,709 A | 4/1989 | Jensen |
| 4,879,996 A | 11/1989 | Harwood, Jr. et al. |
| 4,951,659 A | 8/1990 | Weiler et al. |
| 4,989,597 A | 2/1991 | Werner |
| 5,092,326 A | 3/1992 | Winn et al. |
| 5,165,398 A | 11/1992 | Bird |

(Continued)

OTHER PUBLICATIONS

Lunkenheimer, P.P. et al. "Intrapulmonaler Gaswechsel simulierter Apnoe durch transtrachealen, periodischen intrathorakalen Druckwechsel." *Anacethesist*. 1973. pp. 232-238. vol. 22. Springer-Verlag.

(Continued)

*Primary Examiner*—Justine R. Yu
*Assistant Examiner*—Annette Dixon
(74) *Attorney, Agent, or Firm*—Hodgson Russ LLP

(57) ABSTRACT

A method of delivering a particulate therapeutic agent is disclosed. Such a method may include providing a carbon dioxide scrubber in pneumatic communication with the respiratory system of a patient. Gas and particulate therapeutic agent expired by the patient are passed through the scrubber to provide treated gas, and the treated gas and particulate therapeutic agent are provided back to the respiratory system.

6 Claims, 8 Drawing Sheets

U.S. PATENT DOCUMENTS

Figure 1:
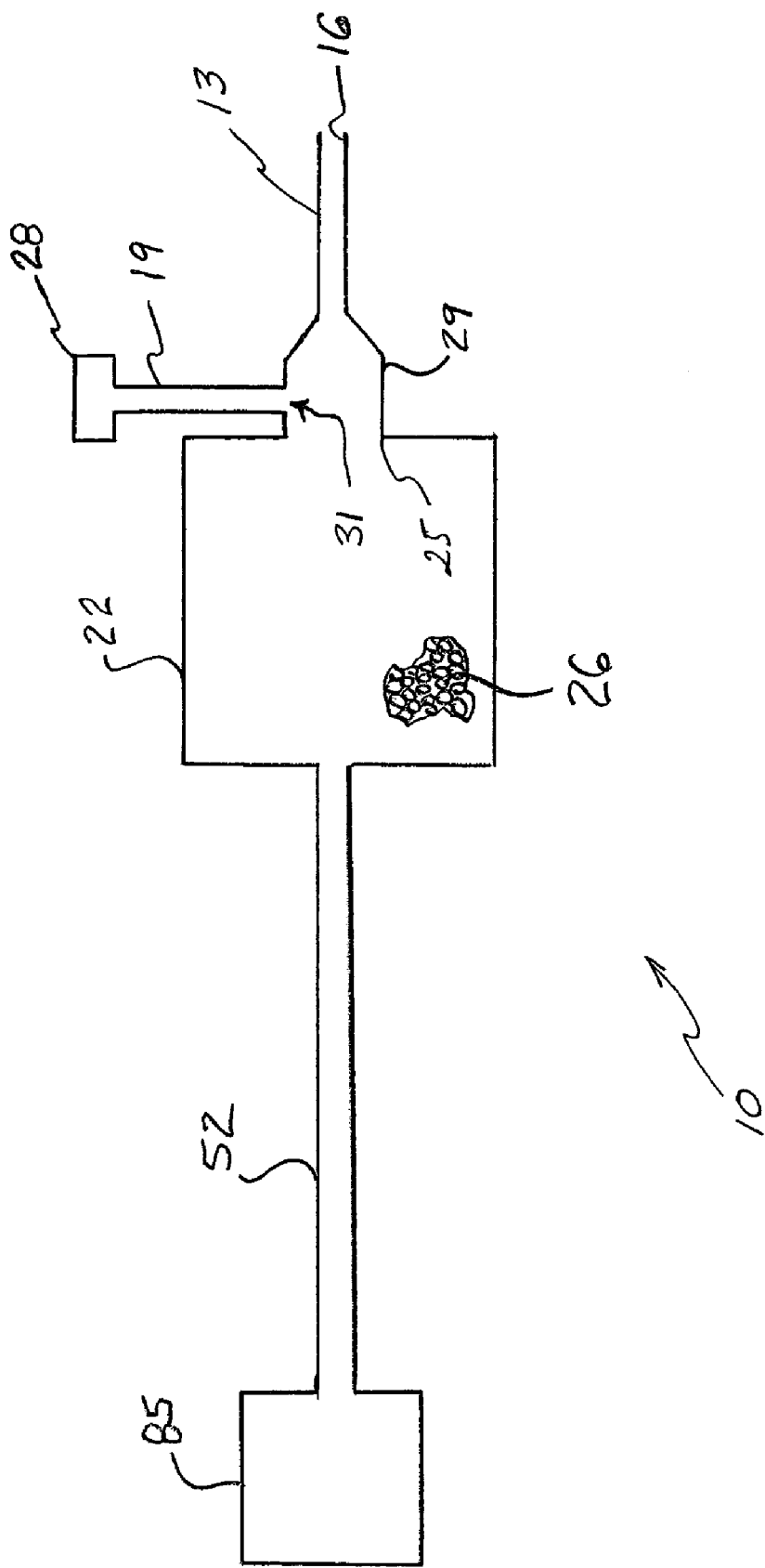
Figure 2:
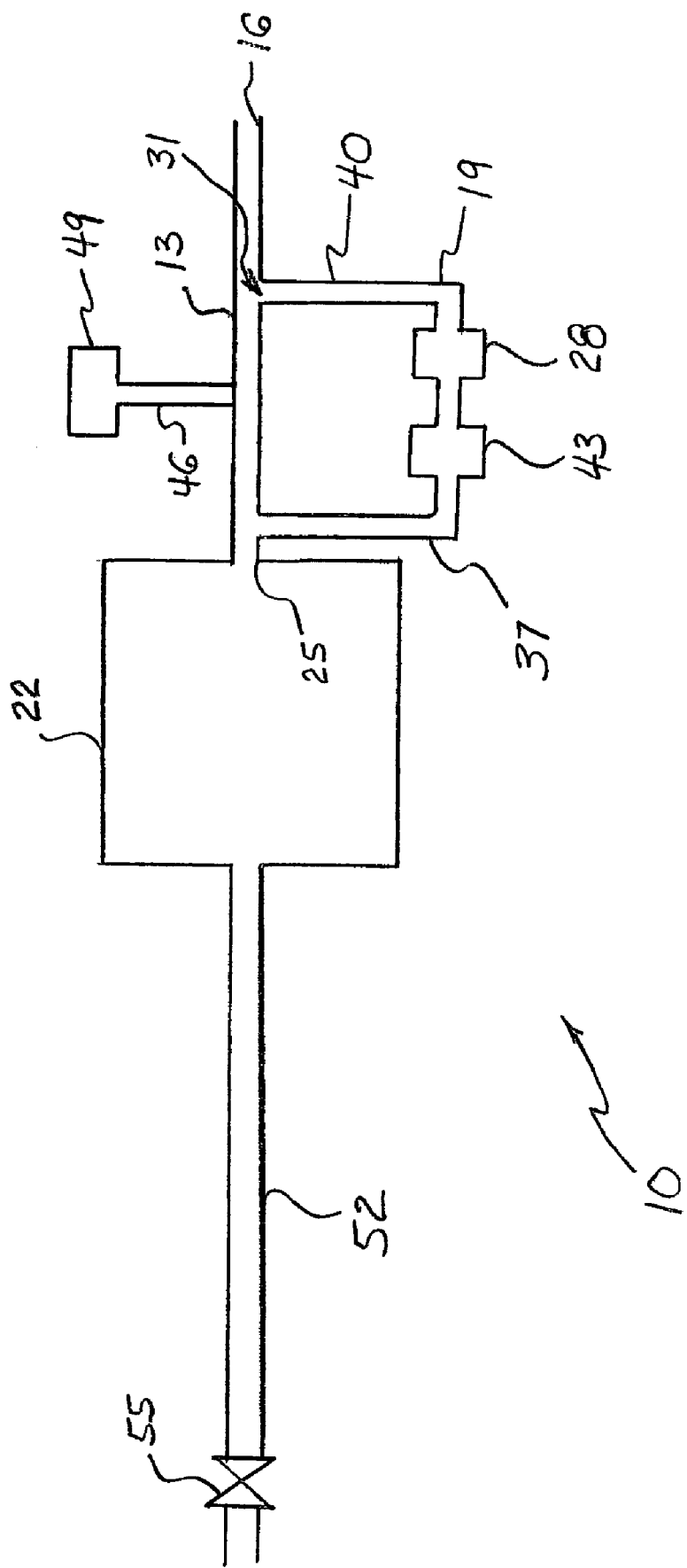
Figure 3:
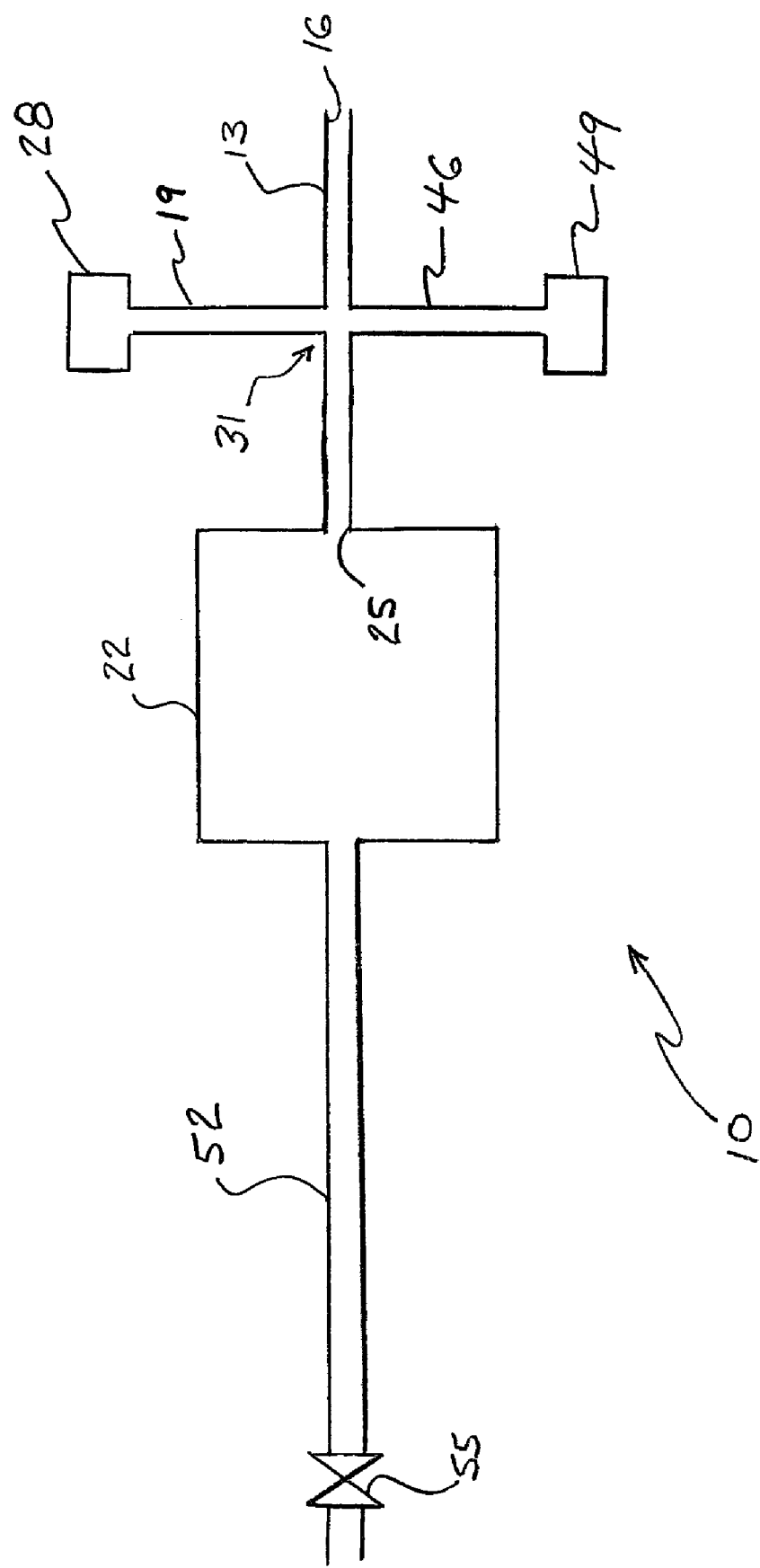
Figure 4:
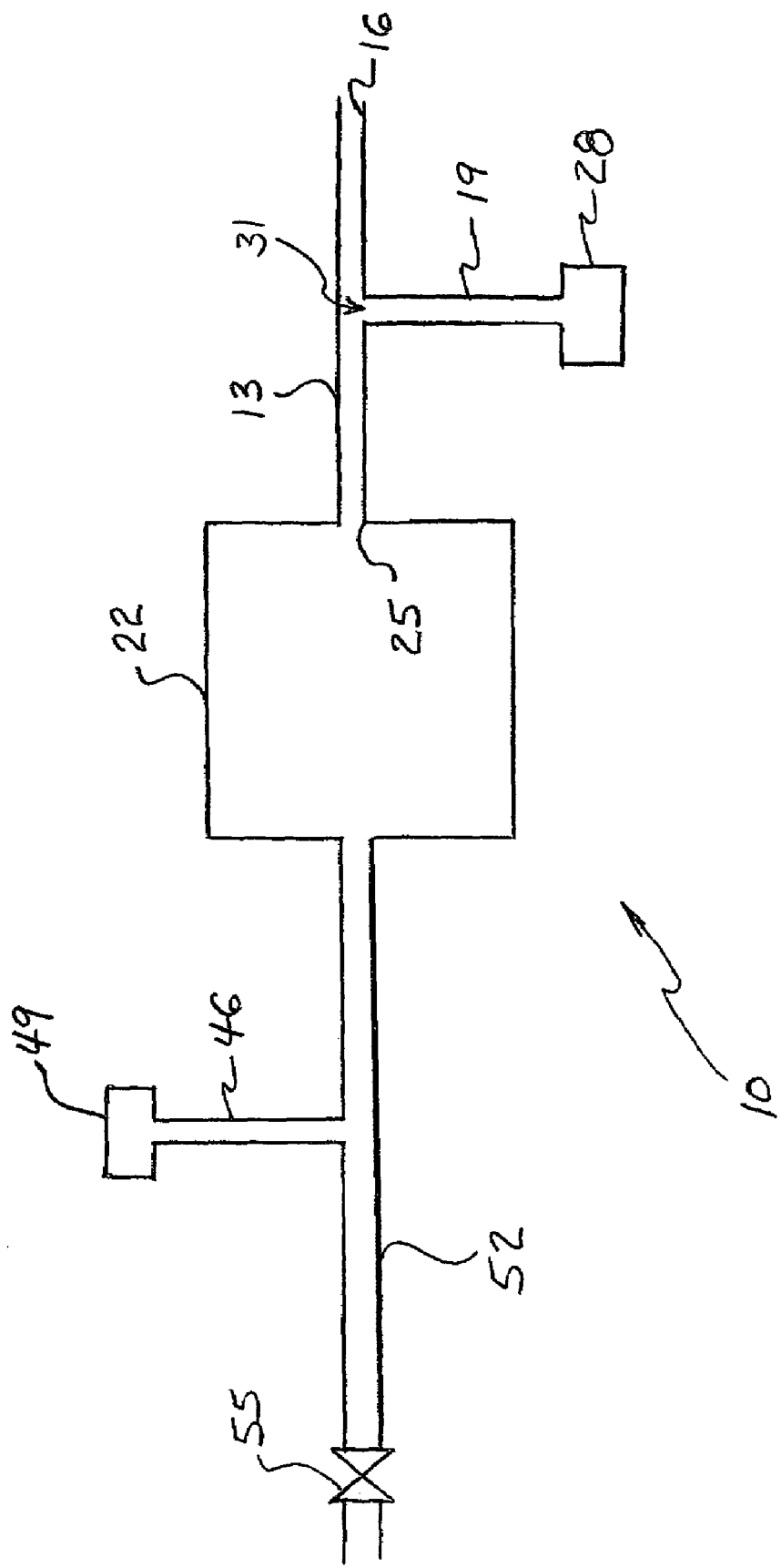
Figure 5:
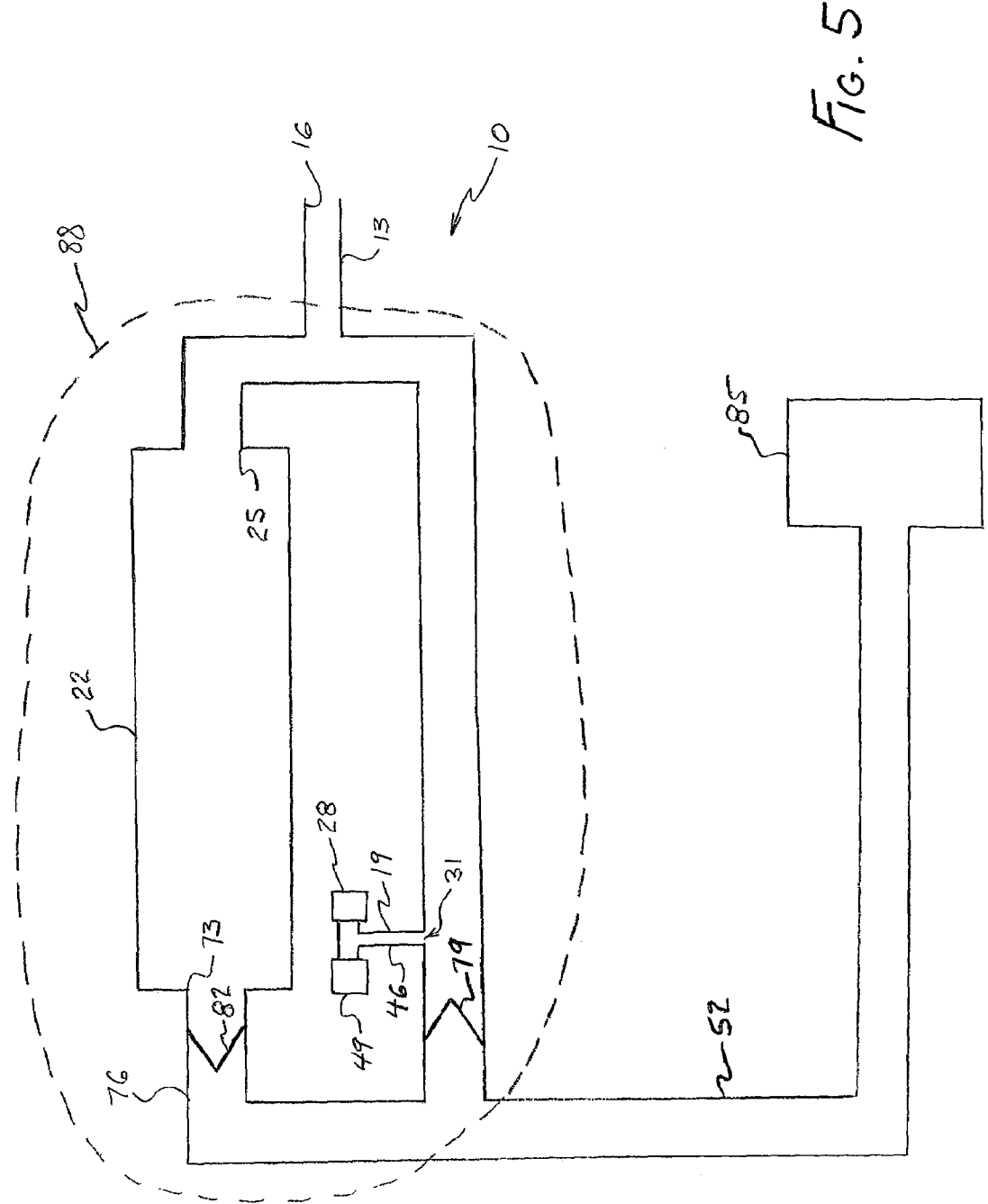
Figure 6:
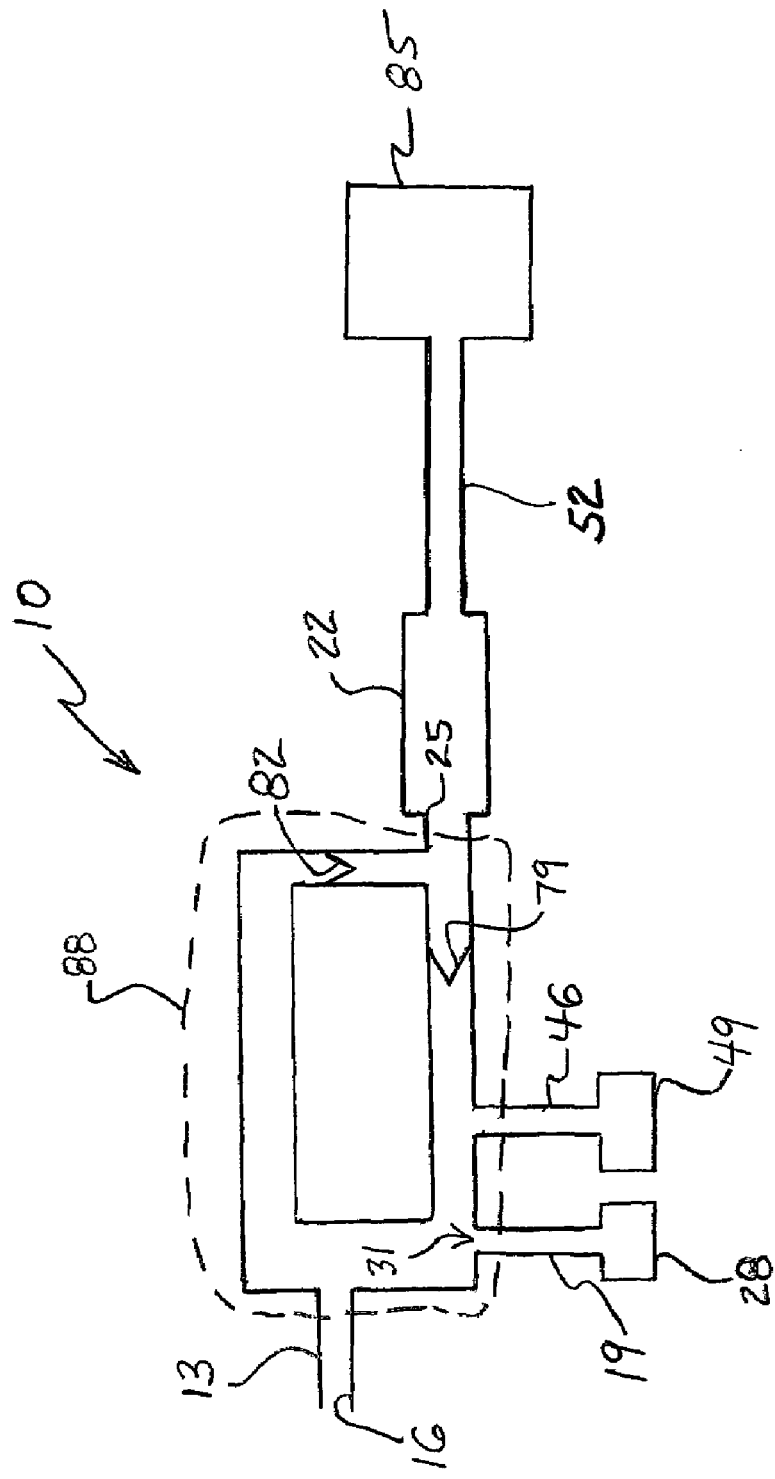
Figure 7:
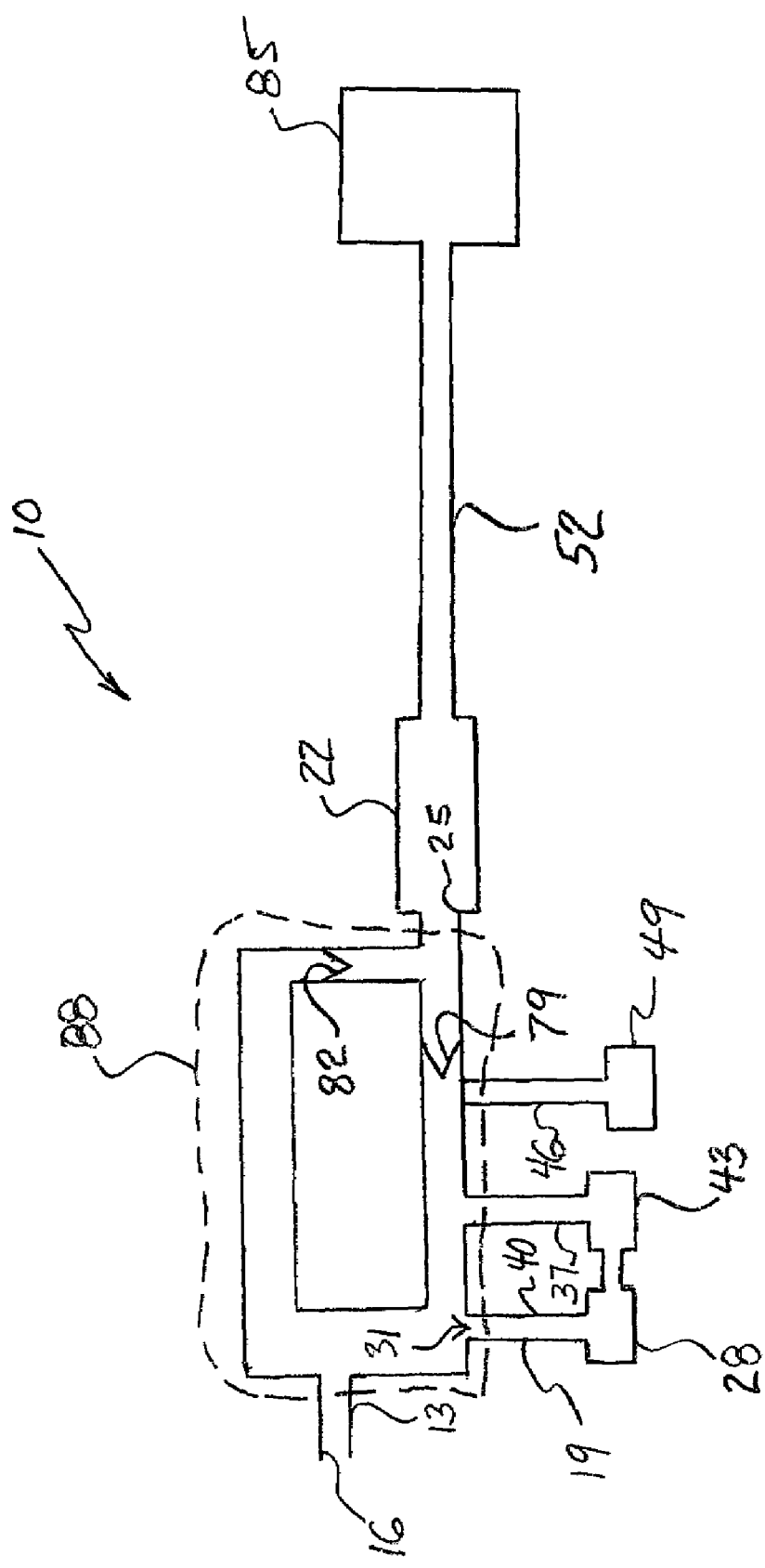

| | | | |
|---|---|---|---|
| 5,299,579 A | | 4/1994 | Gedeon et al. |
| 5,307,794 A | | 5/1994 | Rauterkus et al. |
| 5,335,650 A | * | 8/1994 | Shaffer et al. ......... 128/200.24 |
| 5,485,827 A | * | 1/1996 | Zapol et al. ........... 128/200.14 |
| 5,555,880 A | | 9/1996 | Winter et al. |
| 5,570,683 A | * | 11/1996 | Zapol .................... 128/200.14 |
| 5,590,651 A | * | 1/1997 | Shaffer et al. .............. 600/532 |
| 5,694,924 A | | 12/1997 | Cewers |
| 5,730,119 A | | 3/1998 | Lekholm |
| 5,823,180 A | * | 10/1998 | Zapol .................... 128/200.24 |
| 5,850,835 A | | 12/1998 | Takaki et al. |
| 5,873,359 A | * | 2/1999 | Zapol et al. ........... 128/203.12 |
| 6,041,777 A | * | 3/2000 | Faithfull et al. ....... 128/200.24 |
| 6,095,135 A | * | 8/2000 | Clawson et al. ....... 128/201.13 |

OTHER PUBLICATIONS

Ngeow, Yin K. et al. "A new system for ventilating with high-frequency oscillation." *J. Appl. Physiol.: Respirat. Environ. Exercise Physiol.* 1982. pp. 1638-1642. vol. 53(6). American Physiological Society.

* cited by examiner

THERAPEUTIC AGENT DELIVERY DEVICE AND METHOD

CROSS-REFERENCE TO RELATED APPLICATION

This application claims the benefit of priority to U.S. provisional patent application Ser. No. 60/392,314, filed on Jun. 28, 2002.

FIELD OF THE INVENTION

The present invention relates to methods and devices for delivering therapeutic agents to a patient's lungs.

BACKGROUND OF THE INVENTION

A particulate therapeutic agent may be carried by a carrier gas to a patient's lungs to treat the patient. For example, the carrier gas may be oxygen, and the therapeutic agent may be a liquid particulate or solid particulate. Such a mixture may be an aerosol. Such a mixture may be formed by nebulizing a liquid into the carrier gas. This method of administration may be advantageous when the therapeutic agent targets a specific site of action that is readily accessed by inspiration, or when pulmonary uptake of a therapeutic agent from the systemic circulation is suboptimal, or when systemic blood levels of a therapeutic agent are to be minimized. Examples of therapeutic agents that may be administered in this manner include bronchodilators, steroids, antibiotics, mucolytics, DNA lytic enzymes and genetic vectors for the treatment of lung disease. For example, antifungal and antiviral agents have been administered as aerosols. Further, chemotherapeutic agents for pulmonary malignancy and a host of pulmonary therapies having potential systemic toxicity or undesirable systemic side effects have been nebulized. Additional therapies may include surfactant administration, perfluorocarbon delivery and liposomal drug administration.

The respiratory cycle of a human being is comprised of inspiration and expiration. Inspiration accounts for roughly ¼ of the respiratory cycle and expiration accounts for roughly ¾ of the respiratory cycle. If a therapeutic agent is continuously moved past a patient's mouth, roughly ¾ of the therapeutic agent may not be inspired, and therefore may be wasted. Furthermore, the therapeutic agent that is inspired may be only partially taken up by the lung. For certain therapeutic agents, such as surfactant, more than 90% of inspired therapeutic agent may be subsequently expired (rather than retained in the lung) and thus lost in the expired air. This effect may be greatest when the therapeutic mixture has particulates that are especially small, as may be the case when the therapeutic agent has low surface tension (like surfactant and perfluorocarbon) or is a high density liquid (like perfluorocarbons).

One solution to these inefficiencies of dosing is to rebreathe expired gas, thus renewing the opportunity to take up the therapeutic agent rather than lose it to the environment after expiration. If a "single puff" of the therapeutic agent could be repeatedly rebreathed, ultimate uptake could approach 100%. The same would be true for a "puff" followed by prolonged breath-holding. Repeated rebreathing of the same "puff", or prolonged breath holding may give rise to hypoxia, hypercarbia, discomfort, or may prolong the time required to deliver a requisite dose of the therapeutic agent. Further, a high level of patient cooperation may be required. These problems complicate, if not prevent, use of these approaches to administer a therapeutic agent.

One solution to these problems involves intermittent dosing, in which the therapeutic agent is provided only during inspiration. This solution offers a significant gain in efficiency over continuous dosing, but is still limited in its usefulness by loss of unabsorbed therapeutic agent to the environment during expiration. This solution may be combined with breath-holding to further reduce expiratory losses, but the breath-holding approach may limit the rate of administration of the therapeutic agent and may require a high level of patient cooperation.

SUMMARY OF THE INVENTION

A particulate therapeutic agent delivery device according to the invention may include a respiratory-gas channel, a particulate-therapeutic-agent channel in pneumatic communication with the respiratory-gas channel, a scrubber housing in pneumatic communication with the respiratory-gas channel, and a scrubber material situated within the housing. The scrubber material may be used to remove $CO_2$ from gas expired by a patient. Gas that has been acted on by the scrubber material may be provided to the patient, so that the therapeutic agent is returned to the patient.

In a method according to the invention, a particulate therapeutic agent is provided to the respiratory system of a patient. A carbon dioxide scrubber may be provided in pneumatic communication with the respiratory system, and expired gas from the respiratory system may be provided to the scrubber. The expired gas may be passed through the scrubber to provide treated gas, which may be provided to the respiratory system. By such a method, particulate therapeutic agent which was present in the expired gas may be rebreathed by the patient.

BRIEF DESCRIPTION OF THE DRAWINGS

For a fuller understanding of the nature and objects of the invention, reference should be made to the following detailed description taken in conjunction with the accompanying drawings, in which:

FIG. 1 is a schematic diagram of a therapeutic agent delivery device according to an embodiment of the invention;

FIG. 2 is a is a schematic diagram of a therapeutic agent delivery device according to an embodiment of the invention;

FIG. 3 is a is a schematic diagram of a therapeutic agent delivery device according to an embodiment of the invention;

FIG. 4 is a is a schematic diagram of a therapeutic agent delivery device according to an embodiment of the invention;

FIG. 5 is a is a schematic diagram of a therapeutic agent delivery device according to an embodiment of the invention;

FIG. 6 is a schematic diagram of a therapeutic agent delivery device according to an embodiment of the invention;

FIG. 7 is a is a schematic diagram of a therapeutic agent delivery device according to an embodiment of the invention; and FIG. 8 is a block diagram of a method according to the invention.

DETAILED DESCRIPTION OF THE INVENTION

FIG. 1 is a schematic representation of an embodiment of a particulate therapeutic agent delivery device 10 according to the invention. The delivery device 10 may have a respiratory-gas channel 13 having a patient end 16 to which a patient may be pneumatically connected. The respiratory-gas channel 13 may include an endotracheal tube that may be inserted into the trachea of a patient.

The delivery device 10 may have a particulate-therapeutic-agent channel 19 in pneumatic communication with the respiratory-gas channel 13. An aerosol generator 28 may be provided in pneumatic communication with the particulate-therapeutic-agent channel 19. The aerosol generator 28 may be a nebulizer, for example, a jet nebulizer or an ultrasonic nebulizer. The respiratory-gas channel 13 may include a mixing chamber 29, which may provide a location for the therapeutic agent to disperse and mix with respiratory gas.

A scrubber housing 22 may be in pneumatic communication with the respiratory-gas channel 13. The scrubber housing 22 may include an electrically conductive material so that an electric charge does not develop, and thereby cause therapeutic agent to collect on the scrubber housing 22. The scrubber housing 22 may have an expired-gas orifice 25, which may be used for receiving expired gas from the respiratory-gas-channel 13. A scrubber material 26 may be disposed within the scrubber housing 22. A portion of the scrubber material 26 is illustrated in FIG. 1. The scrubber material 26 may be situated within the scrubber housing so as to receive expired gas via the expired-gas orifice 25. The scrubber material 26 may be soda lime. The scrubber material 26 may be situated so as to remove carbon dioxide from the expired gas to provide treated gas, and so as to provide the treated gas to the respiratory-gas channel 13.

FIG. 1 shows that the particulate-therapeutic-agent channel 19 may be in pneumatic communication with an agent delivery location 31 on the respiratory-gas channel 13. The agent delivery location 31 may be located such that the general flow of gas from the expired-gas orifice 25 to the patient end 16 passes by the agent delivery location 31.

A ventilator 85 may be provided in pneumatic communication with the respiratory gas channel 13. Herein, references to "ventilator" are intended to include devices that provide a force intended to move respiratory gas into a patient via the respiratory gas channel 13. This definition is intended to include devices commonly referred to as a "respirator," as well as devices commonly referred to as a "ventilator." A portion of the ventilator 85, such as a flexible diaphragm or accordion sleeve, may be moved so as to force therapeutic agent in the respiratory-gas channel 13 into the respiratory system.

The ventilator 85 may be in pneumatic communication with an expiratory reservoir 52. The expiratory reservoir 52 may serve to provide an area where gas having therapeutic agent may be stored for future inspiration by the patient.

FIG. 2 is a schematic of an embodiment of the delivery device 10 having a first channel 37 from the respiratory-gas channel 13 to the aerosol generator 28, and a second channel 40 from the aerosol generator 28 to the respiratory-gas channel 13. A pump 43 may be provided within this circuit in order to move gas from the respiratory-gas channel 13, through the aerosol generator 28, and back to the respiratory gas channel 13.

The embodiment of FIG. 2 shows an outlet valve 55 at an end of the expiration reservoir 52. The outlet valve 55 may serve to reduce loss of therapeutic agent from the delivery device 10. The outlet valve 55 may be set to release gas during expiration. The outlet valve 55 may be set so as to keep a pressure inside the delivery device 10 within an acceptable range.

FIG. 3 is a schematic of another embodiment of a delivery device 10 according to the invention. In this delivery device 10, a bias-gas channel 46 is provided in pneumatic communication with the respiratory-gas channel 13. A bias gas source 49 may supply bias gas via the bias-gas channel 46 to the respiratory-gas channel 13. The bias gas may be intended to maintain the partial pressure of oxygen desired for the patient.

FIG. 4 shows the bias-gas source 49 and the bias-gas channel 46 located in a different location from that shown in FIG. 3. The bias-gas channel 46 is shown in pneumatic communication with an expiratory reservoir 52, which may be similar to that described above.

FIG. 5 is a schematic of a delivery device 10 in which the scrubber housing 22 has a treated-gas orifice 73 and the delivery device 10 includes a treated-gas channel 76 situated so as to provide pneumatic communication between the treated-gas orifice 73 and the respiratory-gas channel 13. The area 88 identifies a portion of the device 10 that is referred to as a "circle circuit", so called because there is a pathway along which gas might flow in a circular fashion. An inspiration check valve 79 may be provided in the circle circuit 88, for example near an end of the treated-gas channel 76. The inspiration check valve 79 may be oriented to open during inspiration and close during expiration. The inspiration check valve 79 may be positioned and oriented so as to prevent incompletely scrubbed gas from reentering the respiratory-gas channel, which might otherwise occur during inspiration, to encourage particulate therapeutic agent in the respiratory-gas channel 13 to flow generally toward the patient end 16 during inspiration, encourage treated gas to flow generally away from the expired-gas orifice 25, prevent expired gas from bypassing the scrubber housing 22 during expiration, or any combination of these.

An expiration check valve 82 may be provided in the circle circuit 88. The expiration check valve 82 may be oriented to open during expiration and close during inspiration. The expiration check valve 82 may be positioned and oriented so as to prevent incompletely scrubbed gas from re-entering the respiratory-gas channel, which might otherwise occur during inspiration, to encourage particulate therapeutic agent in the respiratory-gas channel 13 to flow generally toward the patient end 16 during inspiration, encourage treated gas to flow generally away from the expired-gas orifice 25, prevent expired gas from bypassing the scrubber housing 22 during expiration, or any combination of these.

FIGS. 6 and 7 are schematics of other embodiments of a delivery device 10 according to the invention, which include features previously described herein. In FIGS. 6 and 7, the scrubber housing 22 is not within the circle circuit 88. In these embodiments, expired gas may enter the scrubber housing 22 via the expired-gas orifice 25 during expiration, and treated gas exits the scrubber housing 22 via the expired gas orifice 25 during inspiration. Like the delivery device 10 depicted in FIG. 5, the delivery devices 10 in FIGS. 6 and 7 may have the inspiration check valve 79 and the expiration check valve 82 positioned and oriented so as to prevent incompletely scrubbed gas from re-entering the respiratory-gas channel, which might otherwise occur during inspiration, to encourage particulate therapeutic agent in the respiratory-gas channel 13 to flow generally toward the patient end 16 during inspiration, encourage treated gas to flow generally away from the expired-gas orifice 25, or any combination of these.

Figure 8:
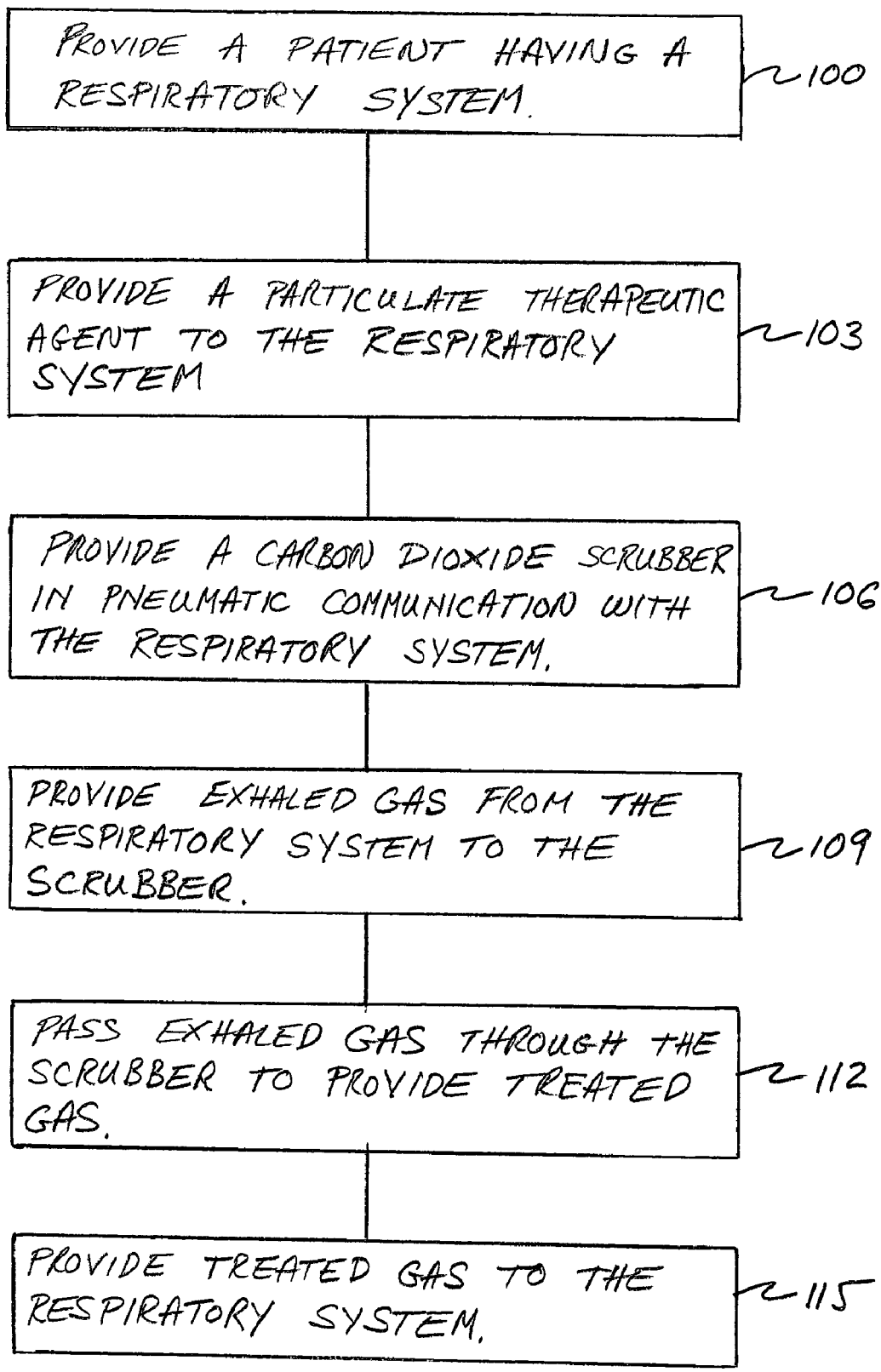

In a method according to the invention, a particulate therapeutic agent may be delivered. FIG. 8 is a block diagram of one such method. In that method, a patient having a respiratory system may be provided 100. A particulate therapeutic agent may be provided 103 to the respiratory system. The therapeutic agent may be provided 103 by nebulizing the therapeutic agent into a gas that is then provided 103 to the respiratory system. A carbon dioxide scrubber may be provided 106 in pneumatic communication with the respiratory system. Expired gas from the respiratory system may be provided 109 to the scrubber, and may be passed 112 through the scrubber to provide treated gas. The treated gas may be thought of as having a lower partial pressure of $CO_2$ than the expired gas. The treated gas may then be provided 115 to the respiratory system. A ventilator may be provided, and portions of the ventilator may be moved in order to force the therapeutic agent into the respiratory system. The ventilator may or may not be in pneumatic communication with the patient.

The method may provide a bias flow of elevated oxygen fraction to prevent hypoxia, while maintaining a low rate of bias flow in order to minimize expiratory waste. At a bias (fresh gas) flow of 10% of the normal minute ventilation, it is believed that only about 6% of expiratory flow escapes a circle circuit according to the invention; the remainder is rebreathed. If the particulate therapeutic agent is added during expiration, it is believed that most of the therapeutic agent administered during expiration is inspired during a subsequent breath, thereby eliminating waste of therapeutic agent during the expiration phase. Hypoxia and hypercarbia are averted. No special breathing maneuvers are required, and the patient remains comfortable.

In a method according to the invention, rebreathing therapeutic agent is used to increase the concentration of the therapeutic agent that is delivered to a patient during inspiration, thereby augmenting both delivery and uptake of the therapeutic agent. This should be contrasted with prior art methods in which rebreathing is used merely to conserve volatile agents and gases during anesthesia. In prior art anesthetic applications, the circle circuit anesthetic concentration is regulated to achieve an alveolar gas concentration desired for anesthesia. In such an anesthetic application, lowering the bias flow reduces the quantity of anesthetic agent required for anesthesia, and is not used to raise the concentration of therapeutic agent in order to enhance uptake by the lungs.

The invention should substantially increase the opportunity for pulmonary absorption of a given amount of therapeutic agent, unless the scrubber or rebreathing circuit removes a large amount of therapeutic agent. To assess the extent to which a rebreathing circuit might remove a therapeutic agent administered as a fine particulate aerosol, we measured the rate of loss of cigarette smoke, which is a fine particulate aerosol, from a soda lime circle circuit. We found that only 11% to 13% of particulate smoke was consumed by the circuit in 3 seconds, the approximate duration of one respiratory cycle. Since the rate of removal of a fine particulate aerosol by the rebreather circuit appears to be low, substantial efficiency should be gained by rebreathing particulate therapeutic agents through a carbon dioxide scrubber. In addition, we have found that by administering smoke into a rebreathing circuit, the concentration of smoke in the air delivered to a model lung was increased seven fold.

A method according to the invention may require little or no patient cooperation. In theory, a method according to the invention may be more efficient than prior art methods of delivering therapeutic agents, and therefore may be more cost effective. Further, a method according to the invention may be used during prolonged dosing of both spontaneously breathing patients and mechanically ventilated patients.

Non-rebreathing aerosol administration is safe for the patient breathing room air. However, the rebreathing method described in this application might not be used safely without an elevated fraction of inspired oxygen. Therefore, the method may be limited to patients having access to oxygen or to oxygen enriched gas mixtures.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method of delivering a particulate therapeutic agent, comprising:
   (a) providing a patient having a respiratory system;
   (b) providing a dose of particulate therapeutic agent to a gas, and delivering the agent and the gas to the respiratory system;
   (c) providing a carbon dioxide scrubber in pneumatic communication with the respiratory system;
   (d) providing gas expired from the respiratory system, and particulate therapeutic agent expired from the respiratory system;
   (e) passing the expired gas and expired particulate therapeutic agent through the scrubber to treat the expired gas, and thereby provide treated gas;
   (f) passing the expired gas and expired particulate therapeutic agent out of the scrubber to provide treated gas; and
   (g) providing the treated gas and expired particulate therapeutic agent to the respiratory system;
   (h) repeating (d) through (g), until the expired particulate therapeutic agent carried by the gas is substantially absorbed.

2. The method of claim 1, further comprising:
   providing a ventilator; and
   moving the ventilator to force the therapeutic agent into the respiratory system.

3. The method of claim 1 wherein providing the therapeutic agent includes nebulizing the therapeutic agent.

4. The method of claim 1, wherein the particulate therapeutic agent is a liquid.

5. The method of claim 1, wherein the particulate therapeutic agent is a solid.

6. The method of claim 1, further comprising providing oxygen to the patient.

* * * * *